United States Patent [19]

Soon-Shiong

[11] Patent Number: 5,739,033
[45] Date of Patent: Apr. 14, 1998

[54] PHYSIOLOGICAL CELL SEPARATION AND METHOD OF SEPARATING CELLS USING SAME

[75] Inventor: Patrick Soon-Shiong, Los Angeles, Calif.

[73] Assignee: Vivorx, Inc., Santa Monica, Calif.

[21] Appl. No.: 486,404

[22] Filed: Jun. 5, 1995

Related U.S. Application Data

[63] Continuation of Ser. No. 220,579, Mar. 31, 1994, abandoned, which is a continuation of Ser. No. 876,830, Apr. 27, 1992, abandoned, which is a continuation of Ser. No. 582,650, Sep. 14, 1990, abandoned, which is a continuation-in-part of Ser. No. 410,091, Sep. 20, 1989, abandoned.

[51] Int. Cl.$^6$ ............................................. C12N 5/00
[52] U.S. Cl. .................. 435/325; 435/404; 435/366
[58] Field of Search ............................ 435/240.2, 240.1, 435/240.3, 325, 404, 366

[56] References Cited

U.S. PATENT DOCUMENTS 4,640,785  2/1987  Carroll et al. ............................ 210/782

FOREIGN PATENT DOCUMENTS 0191613  8/1986  European Pat. Off. ............ 435/240.1

OTHER PUBLICATIONS

Raydt. Hoppe–Seyler's Z. Physiol. Chem. vol. 358, pp. 1369–1373, 1977.
D'Allessandro et al. Diabetes vol. 38, pp. 7–9, 1989.
Lake et al. Diabetes. vol. 38, pp. 143–145, 1989.

*Primary Examiner*—John W. Rollins
*Assistant Examiner*—Christopher R. Tate
*Attorney, Agent, or Firm*—Gray Cary Ware & Freidenrich; Stephen E. Reiter

[57] ABSTRACT

An aqueous composition, initially present as a two-phase gradient, useful for separation of two cell types, such as islet cells from acinar cells, is disclosed, as well as a method of separating the cells. The composition is comprised of a water soluble, metabolically inert substance which maintains density, osmolarity and pH in the presence of cells, and a physiological cold storage solution comprising viscosity modifiers to increase the viscosity and osmotically active impermeant agents for suppressing cold-induced cellular edema, and also comprising a physiological solution capable of maintaining viable cells. These solutions are present in various combinations in a concentration sufficient to provide a first solution with a density greater than both cell types in their natural state, and less than the second cell type after incubation in said solution, and a second solution having a density less than that of both cell types. The system is allowed to stand or is centrifuged to separate the cells.

6 Claims, 5 Drawing Sheets

PHYSIOLOGICAL CELL SEPARATION AND METHOD OF SEPARATING CELLS USING SAME

This application is a continuation of U.S. application Ser. No. 08/220,579, filed Mar. 31, 1994, now abandoned, which is in turn a continuation of U.S. application Ser. No. 07/876, 830, filed Apr. 27, 1992, now abandoned, which is in turn a continuation of U.S. application Ser. No. 07/582,650, filed Sep. 14, 1990, now abandoned, which is in turn a continuation-in-part of U.S. application Ser. No. 07/410, 091, filed Sep. 20, 1989, now abandoned, the entire contents of each of which are hereby incorporated by reference herein.

FIELD OF THE INVENTION

This invention relates to the fields of cell biology and medicine, and more particularly, to the field of mammalian cell separation of, particularly for insulin-producing cells.

ART BACKGROUND

Isolation and purification of a specific cell population is an important issue in many areas of cell biology. Several methods of purification of cells have been used over the years, including centrifugal separation based upon size or density, cloning and immunological (antibody) recognition and separation, among others.

Over the years, many different compounds have been used to form density gradients to enable particles to be separated according to their size and/or buoyant density. Some common materials for this purpose include ficoll®, percoll®, cesium chloride and dextran. While these materials may have been used for the separation of cells, they have certain drawbacks which make them not particularly well-suited for this task. These drawbacks are due in part to sensitivity of the cells to high osmotic or ionic stress, sensitivity to the toxic compounds used, and stability of the separation compounds to autoclaving or other sterilization techniques.

When cells are separated using centrifugation, they may be separated by size or buoyant density, or to a minor extent, by charge or other related external surface characteristic. With respect to separation processes relying upon differences in size, when particles in solution are subjected to a centrifugal field, they move in the direction of the force applied, and in general, larger particles will move faster than smaller particles. Therefore, when cells differ greatly in size, a reasonable purification may be obtained by low speed centrifugation in a suitable medium.

In cell suspensions containing a mixed population of cells, cells of similar sizes may have different buoyant densities, whereas cells of different sizes may have the same densities. Cells having different buoyancy characteristics may be separated on a density gradients, such as continuous gradients or discrete step (discontinuous) gradients. In either case, the principle is that the cells will migrate through the gradient medium until they reach a point where the density of the medium equals the density of the cells, in the case of a continuous gradient, or where the cells are sandwiched at the interface in between a medium having a lower density and a medium having a greater density than the cells, in the case of a discontinuous gradient. This method results in the cells being disposed in discrete bands within between the media.

An example of the need for rapid isolation and purification of cells is the desirability of acquiring large quantities of pure insulin producing cells from a pancreas for purposes of transplanting them into a diabetic patient. The pancreas is the organ responsible for insulin production. Specifically, insulin is produced and regulated by areas of the pancreas known as the Islets of Langerhans, referred to herein as islet cells or islets, which are the endocrine cells of the pancreas. Such cells comprise a small percentage of the pancreas (around 2%). The major cellular component of the pancreas consists of exocrine tissue including acinar and ductal cells, and it has been shown to be a formidable task to purify the islet cells from the acinar cells. Gray and Morris, Transplantation (1987) 43:321.

Islet cell isolation and purification is currently being performed by density gradient separation based upon the principle of density differences between the isolated islets and the acinar cells. Generally the dispersed pancreatic preparation is placed in a discontinuous density gradient solution containing ficoll®, percoll® or dextran, all well-known density gradient materials. There are several disadvantages to prior art methods of islet cell isolation and preparation utilizing such materials. For one, the method is cumbersome, time consuming and labor intensive since several gradients are required to be layered and the islets must be carefully removed from within these multiple gradients. Another disadvantage is that the method yields inconsistent results since the density of the islet cells and acinar cells may change during the process as a result of edema in the cells caused by the materials used in the separation. Another serious disadvantage of the prior art methods is that the cells are subjected for substantial periods of time to the gradient material which may be toxic, and is at least detrimental to the viability of the cells. This is particularly the case because the currently used gradient solutions such as ficoll®, percoll® and dextran are not physiological solutions thus causing both osmotic and ionic stresses on the cells. Ficoll® is known to be toxic to cells as well as mutagenic. Percoll® also causes cellular damage. Dextran in the concentrations used in gradient separation may cause cellular damage as a result of the osmotic stresses applied to the cells. Furthermore, none of the gradient separation materials are capable of preserving cells for any substantial periods of time.

SUMMARY OF THE INVENTION

The present invention comprises a cell separation material useful in the separation and purification of cells, particularly islet cells, and a method of cell separation using the invented material. The material has properties and characteristics of a physiological solution and therefore is not harmful and is even somewhat beneficial to the cells. Moreover, it has cell preservation properties, being derived in part from a tissue preservation solution.

The invented material is capable of separating two mixed types of cells, such as acinar and islet cells, without being entirely dependent upon the naturally occurring densities of the respective cells. Moreover, the multiple gradients required in the prior art separation techniques are not required in the present invention in that an initially two phase aqueous separation system is capable of performing the desired separation.

The composition of this invention is made of heat stable material. This facilitates sterilization by allowing autoclaving.

The present invention is a composition comprising two aqueous phases, as well as a continuous gradient which develops between the two phases, of solutions useful in the isolation and purification of two types of cells from a mixture. In particular, this invention is useful in separating islet cells from a pancreatic tissue digestate containing acinar cells in addition to the islets. The composition permits high viability of at least one type of cells, such as the islet cells, especially under cold conditions (such as 4° C.), and permits these cells to be fully biologically active after the separation. The present invention also comprises a method of isolating and purifying islet cells using the composition.

DETAILED DESCRIPTION OF THE INVENTION

Figure 1:
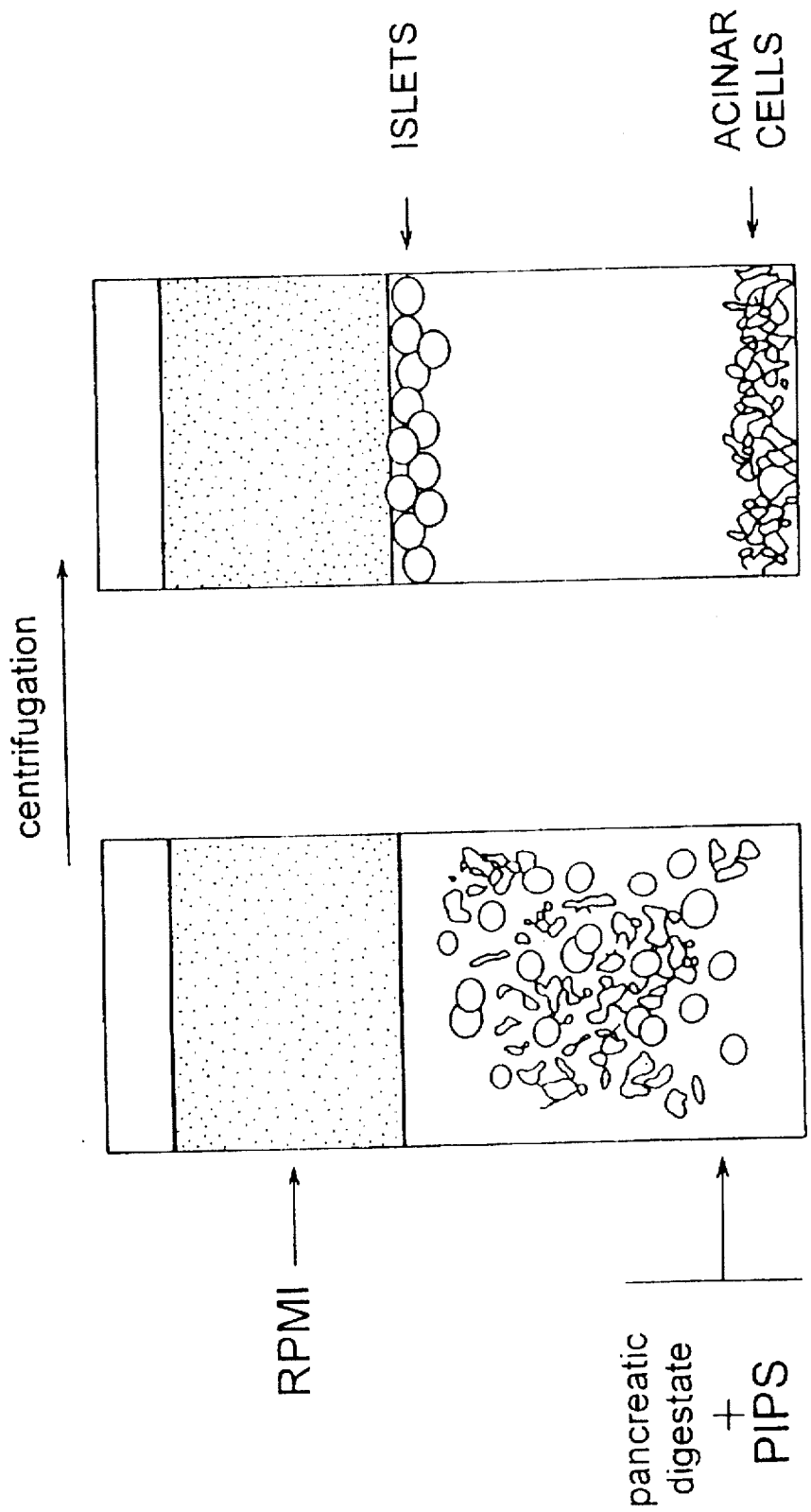
FIG. 1 is a schematic view of the method of the present invention.

Both initial phases of the composition can be made from the same solution, but with different densities. This solution is a combination of a density gradient component and an organ preservation solution comprising an osmolarity adjusting agent and a viscosity modifier.

The density gradient component is a water soluble, metabolically inert substance which maintains density, osmolarity and pH in the presence of cells, and is useful in gradient separation. An example is 5-(N-2,3-dihydroxypropylacetamido) 2,4,5-tri-iodo-N,N'-bis(2,3-dihydroxypropyl)isophthalamide sold under the trademark Nycodenz® by Nycomed AS of Norway and Robbins Scientific (Mountain View, Calif.). This material has a molecular weight of 821 g/mole and a density of 2.1 g/ml. It is very soluble in water and its osmolarity is near physiological. Unlike ficoll® and percoll®. 5-(N-2,3-dihydroxypropylacetamido) 2,4,5-tri-iodo-N,N'-bis(2,3 dihydroxypropyl)isophthalamide is non-toxic to cells and is heat stable, even in solution, making it autoclavable for purposes of sterilization. Another water soluble, metabolically inert substance which may be used in the present invention is a tri-iodinated benzamide derivative of glucose sold under the name Metrizamide®, also available from Nycomed AS of Norway and Robbins Scientific (Mountain View, Calif.).

The 5-(N-2,3-dihydroxypropylacetamido) 2,4,5-tri-iodo-N,N'-bis(2,3-dihydroxypropyl)isophthalamide or other water soluble, metabolically inert material is dissolved in solution. The aqueous solution in which the water soluble, metabolically inert material is dissolved has a viscosity modifier comprising one or more colloids or polymers so that the solution has a viscosity in the range of approximately 1.5 to 3.2 mPa.s (milli-Pascal second; 1 mPa.s= centipoise). Such viscosity modifiers include colloids such as hydroxyethyl starch or serum albumin, or polymers such as polyethylene glycol, dextran and alginate. Alginate can be used in concentrations ranging from 0 to 2.5% of the solution to provide the required viscosity of the solution.

The solutions can be isotonic to the cells to be separated. However, in one aspect of the invention, the second of the two types of cells in the mixture to be separated is more permeable than the first. In this case, if the solutions are somewhat hypertonic, this more permeable second cell type will increase in density with incubation in the hypertonic solution. This aids separation of the two cell types by increasing the difference in density of the two cell types. For example, when the first cell type is islet cells and the second cell type is acinar cells, the acinar cells can preferentially be made more permeable by directing collagenase enzymes to acinar cells via ductal injection of the enzymes. The acinar cells then increase in density with incubation, aiding in cell separation. The islet cells, on the other hand, are preserved in their natural state and are kept viable by this procedure. To effect separation of the cells after incubation, the density of the solution for use in the lower phase of the gradient is made to be heavier than the density of the second type of cells in their natural state, but lighter than the density of the second cell type after they incubate in this solution.

When the solution is made in the range of approximately 290–320 mOsm, which is at or very close to the physiological range of osmolarity for most cells, the yield of the desired, less permeable cells is optimized. At an osmolarity of somewhat higher levels, i.e. between approximately 320 and 550 mOsm, purity of the desired less permeable cells is optimized. Therefore, in order to achieve a reasonable level of both purity and yield, a range of approximately 320 to 440 mOsm is preferred.

Osmotically active impermeants are osmolarity enhancing compounds which do not permeate into the cells. Such materials are useful in providing a physiological environment for cells without causing cell edema to the preferred cell type, whereas, traditional gradient separation materials contribute to cell edema in all cells exposed to those materials. Osmotically active agents which are beneficial in the invented solution include sugars such as glucose, mannitol, sucrose, anions such as phosphate, sulfate, glycerophosphate, citrate and gluconate, and compounds which specifically prevent or suppress cold-induced edema such as lactobinic acid or raffinose. Organ preservation solutions which could be used are Eurocollins and UW solutions. UW solution, in particular, has been reported as an organ preservation solution for liver and pancreas transplantation (Lancet 7:617–619, 1988) obtained from DuPont Critical Care (Waukegan, Ill.). UW solution is comprised of the following components:

| Ingredient | Concentration/liter |
| --- | --- |
| K lactobionic | 100 mmol |
| $NaKH_2PO_4$ | 25 mmol |
| Adenosine | 5 mmol |
| $MgSO_4$ | 5 mmol |
| Glutathione | 3 mmol |
| Raffinose | 30 mmol |
| Allopurinol | 1 mmol |
| Insulin | 100 U |
| Trimethoprim/sulphamethoxazole | 8 mg/ |

-continued

| Ingredient | Concentration/liter |
| --- | --- |
| Modified hydroxyethyl starch | 40 mg |
| | 50 g |
| Na | 30 mmol/l |
| K | 120 mmol/l |
| pH | 7.4 |
| | 320–330 mmol/l |

The first, or lower, solution has a density somewhat greater than the density of both cell types in their natural state, in the range of 1.097 to 1.126 g/ml for islet-acinar cell separation. This density will prevent the preferred cells, such as the islets, from entering the lower phase of the gradient. The cells of the second type, which are somewhat permeable to the solute in which they are incubating, as well as cells which are no longer viable due to the preferential degradation through the use of enzymes such as collagenase, become more dense than in their natural state through uptake of the solute. These cells will then enter the lower phase. The lower phase should be at a density at or slightly lighter than the heavier cells become after incubation, so that the heavier cells will in fact fall through the lower phase and settle at or near the bottom of the container. One means to determine the appropriate density for the lower layer is to incubate a crude prep of the heavier cells in various densities of the solution that forms the lower layer. Observing these incubating cells after a period of time long enough for the cells to change in density will show which density is appropriate for the lower phase of the gradient.

The upper phase of the two phase aqueous solution can be made of the same solution as the lower phase, but at a different density. Alternatively, the upper phase can be a physiological solution containing nutrients, such as a culture medium like RPMI, Hank's solution, MEM, Eagles medium, or the like. When the upper phase is made of a different density version of the same solution as the lower phase, a small, third layer of physiological solution is preferably added as an uppermost layer to trap any fat cells contained in the mixed population, such as from tissue digestate.

The density of the upper phase is less than that of both cell types, and for islet-acinar separation is less than 1.050, preferable less than 1.008, and most preferably around 1.004 g/ml. The greater the difference between the densities of the initial two phases of the gradient, the wider the continuous gradient is that forms during separation. This wider continuous gradient region will allow better separation of the two cell types.

As noted above, the subject invention also comprises a method of isolating and purifying one population of cells, such as islet cells, using the invented two phase aqueous solution. The invented method comprises generally the steps of (1) obtaining a mixture of cells, such as a pancreatic digestate, preferably in a manner which preferentially slightly damages one population of cells, such as acinar cells, making them more permeable, (2) combining the mixture of cells in the bottom (first) solution in a container such as a centrifuge tube, (3) adding the second solution to the container, with an optional third uppermost layer, as described previously, and (4) allowing separation, either by standing or centrifuging at a low speed for a sufficient time and speed to obtain separation of the two cell types, such as acinar from islet cells, with the denser, or second, cell type, such as damaged or non-viable acinar cells, migrating to or near the bottom of the tube and the lighter, or first, cell type, such as islet cells, collecting at or near the interface between the two solutions. During this separation a short, continuous gradient forms between the two discrete phases, providing a range of densities intermediate between those of the two original phases. The lighter or first type of cells, such as the islet cells, collect at the density within this continuous gradient corresponding to their internal density. Finally, (5) cells of the first, or desired type, such as islet cells, are removed from the gradient where they have formed a band. With an islet-acinar mix, the purity of the islet cells is very high, and may be in the range of 85% to 95%, depending on the preparation and technique.

For islet-acinar separation, the pancreatic tissue may be obtained from any pancreas containing animal, such as pig, cow, dog, rat, monkey or human. The pancreatic tissue is obtained from the donor animal and then digested into a cell suspension by any of various methods known in the art such as the method described in Warhock, et al, *Transplantation*, 45:957–963, No. 5, May, 1988. These procedures utilize ductal injection of collagenase to preferentially damage acinar cells, which are present surrounding the ducts. The pancreatic tissue is preferably maintained at 4° C. or similar cold temperature during the entire isolation and purification process to ensure that the enzymes contained in the acinar cells do not have an opportunity to lyse the islet cells.

The mixed population of cells, such as pancreatic tissue digestate so obtained, is suspended in the first solution which is preferably 5-(N-2,3-dihydroxypropylacetamido) 2,4,5-triiodo-N,N'-bis(2,3-dihydroxypropyl)isophthalamide in UW solution. The mixed population such as the pancreatic tissue is first suspended in about 1 to 5 ml of physiological Hank's or similar aqueous material and then mixed into a volume of the first solution to create the appropriate density. Any container appropriate for the separation of gradient layers can be used. If one rat pancreas is used, about 15 ml of the first solution can be used in a 50 ml centrifuge tube, and if one canine pancreas is used about 150 ml of the first solution can be used in a 250 ml tube.

The second solution, preferably RPMI, is then added to the container. At least approximately ¼ of the volume of the first solution is layered over the first solution. The gradient can then be allowed to incubate at 1 g for a period of at least 30 minutes, or until the heavier cells, e.g. the acinar cells, separate and fall to or near the bottom of the container. Alternatively, the container can be centrifuged, preferably for 15 minutes at 4° C. at a speed sufficient to create a centrifugal force that does not damage the first, or desired cell type, preferably at a speed sufficient to create a centrifugal force at the interface between the first solution and second solution up to around 180 g. The lighter cells, e.g. the islet cells, are then removed from at or near the interface. The lighter cells thus obtained are a relatively pure culture, being free from the heavier cells, and being relatively viable and healthy.

FIG. 1 shows a general schematic step diagram of the invented method. The term PIPS stands for the physiological islet purification solution, or the first solution of the present invention. In the pancreatic digestate, the dark circles represent the islet cells and the smaller irregularly shaped objects are the acinar cells in the mixed population of the digestate.

A description of a non-limiting exemplary method of the present invention follows. A 50 ml tube containing rat pancreatic tissue was subjected to centrifugation in accordance with the present invention. After centrifugation, the 50 ml tube contained the two phase aqueous solutions with the islet cells disposed at the interface and the acinar cells disposed at the bottom of the tube. A microscopic view of the cells taken from at or near the interface shows that only the islet cells are present at the interface. A microscopic view of the cells taken from the bottom of the tube shows that only acinar cells are present at the bottom of the tube.

Several experiments were performed to demonstrate the effectiveness of the subject invention.

Experiment 1

Comparative In Vitro Viability

Islet cells were isolated, hand-picked and separated into three groups. Equal numbers of cells were incubated for 30 minutes at 4° C. into three different solutions, RPMI, PIPS and ficoll. The PIPS and ficoll were both dissolved into UW solution. Both populations were removed from their respective incubation solutions and placed in a physiological solution to measure the cell function in terms of insulin production. The cells were incubated in specified glucose solutions of 60 mg %, which is physiological base line, and 300 mg % which is elevated, and which should induce full cellular production of insulin. The cells were then returned to the 60 mg physiological basal level of glucose. As can be seen from the following Table 1, the cells incubated in PIPS produced over twice the insulin (10.4 compared with 4.6) as the ficoll incubated cells. The numbers in parenthesis are the stimulation index, that is, the ratios between the insulin production compared with the baseline value at the first 60 mg % incubation.

TABLE 1

| Incubation Sln. | INSULIN in µUnits/ml (ratio to baseline) | | |
| --- | --- | --- | --- |
| | Glucose 60 mg % | Glucose 300 mg % | Glucose 60 mg % |
| RPMI | 9.7 (1.0) | 15.0 (1.8) | 14.2 (1.5) |
| PIPS | 6.8 (1.0) | 70.8 (10.4) | 26.6 (3.9) |
| Ficoll | 7.2 (1.0) | 32.9 (4.6) | 23.9 (3.3) |

Experiment 2

Transplantation of Purified Human Islets

Human islets were isolated in accordance with this invention. A nude rat was transplanted with 4000 human islets in a blood clot under the renal capsule. Four weeks post-transplant, the rat was anesthetized and cannulated for systematic blood sampling. Heparinized saline (10 units/ml) was used in the cannula to replace blood volume and 0.3 to 0.4 ml of blood was removed at time 0, 5, 15, 30, 45 and 60 minutes after glucose injection of 3 mg/g of body weight. Plasma was frozen for subsequent RIA of insulin and blood glucose measurements in accordance with procedures known in the art. Blood was analyzed in duplicate. The results are set forth in Table 2 below. The table shows the insulin and blood glucose concentrations from the experiment at the specified time intervals. As can be seen, high levels of insulin release occur in response to glucose stimulation, demonstrating excellent viability of islets isolated in the invented solution utilizing the invented method.

TABLE 2

| Time (min) | Insulin (ng/ml) | Blood Glucose (mg/dl) |
| --- | --- | --- |
| 0 | 0.774 | 212 |
| 5 | 1.120 | 336 |
| 15 | 1.167 | 408 |
| 30 | 2.585 | 498 |
| 45 | 2.911 | 467 |
| 60 | 3.585 | 590 |

Experiment 3

Transplantation of Purified Dog Islets

Figure 2:
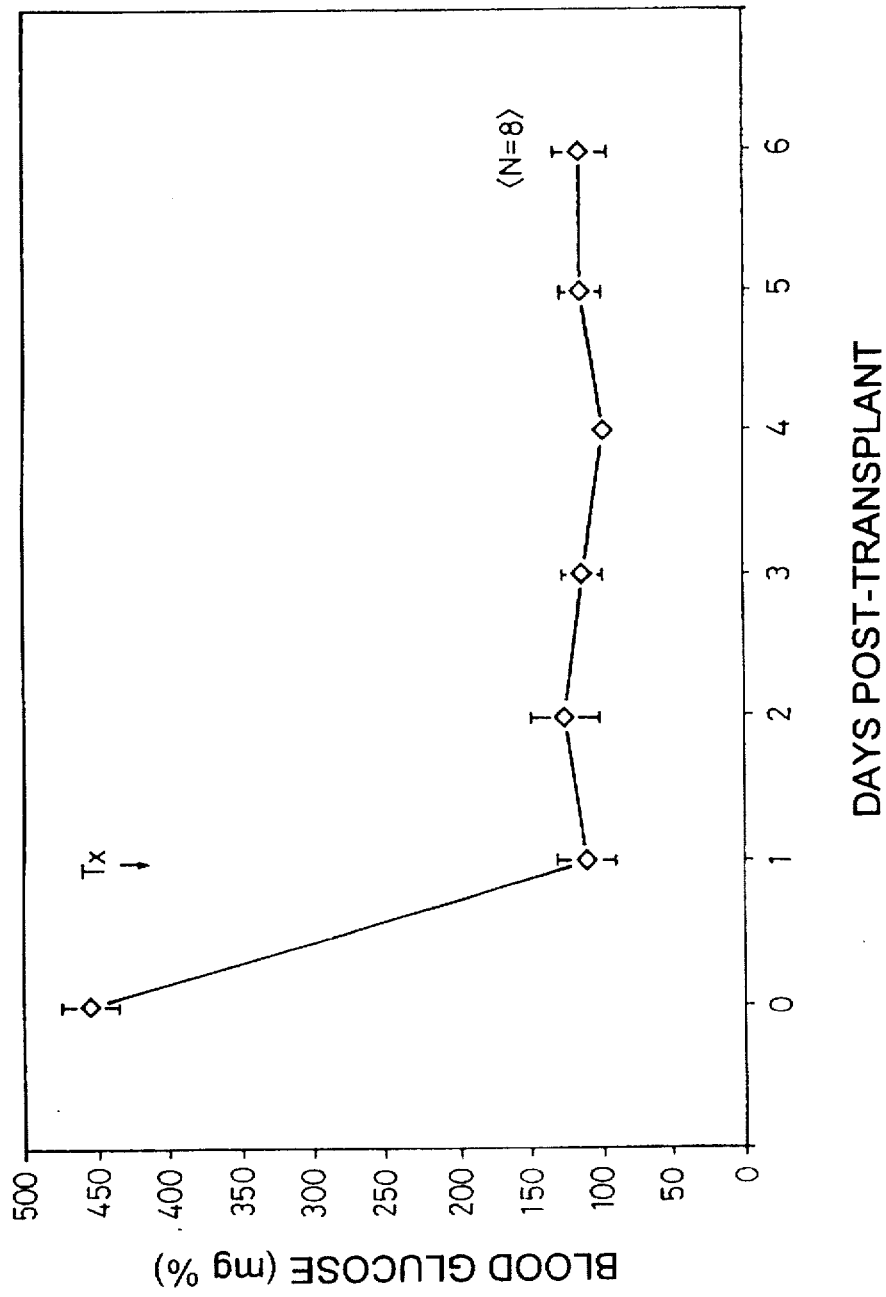
FIG. 2 is a graph demonstrating the viability and effectiveness of islet cells obtained by the invented method, which cells were obtained from canine pancreatic tissue and implanted into diabetic rats.

Islet cells obtained from canine pancreas in accordance with the present invention were encapsulated in accordance with procedures described by Lim and Sun in order to prevent immunological rejection due to histocompatibility differences resulting from the use of the cells in a different species. The encapsulated islets were then transplanted into a diabetic Lewis rat. The blood glucose levels were then monitored on a daily basis. As shown by FIG. 2, the initial blood glucose level was greater than 450 mg %. After transplantation of the encapsulated islets, the level dropped to approximately 100 mg % and remained at that level for the 6 days for the experiment, demonstrating in vivo viability of the canine islets isolated using the present invention.

Experiment 4

Longterm In Vivo Viability

Figure 3:
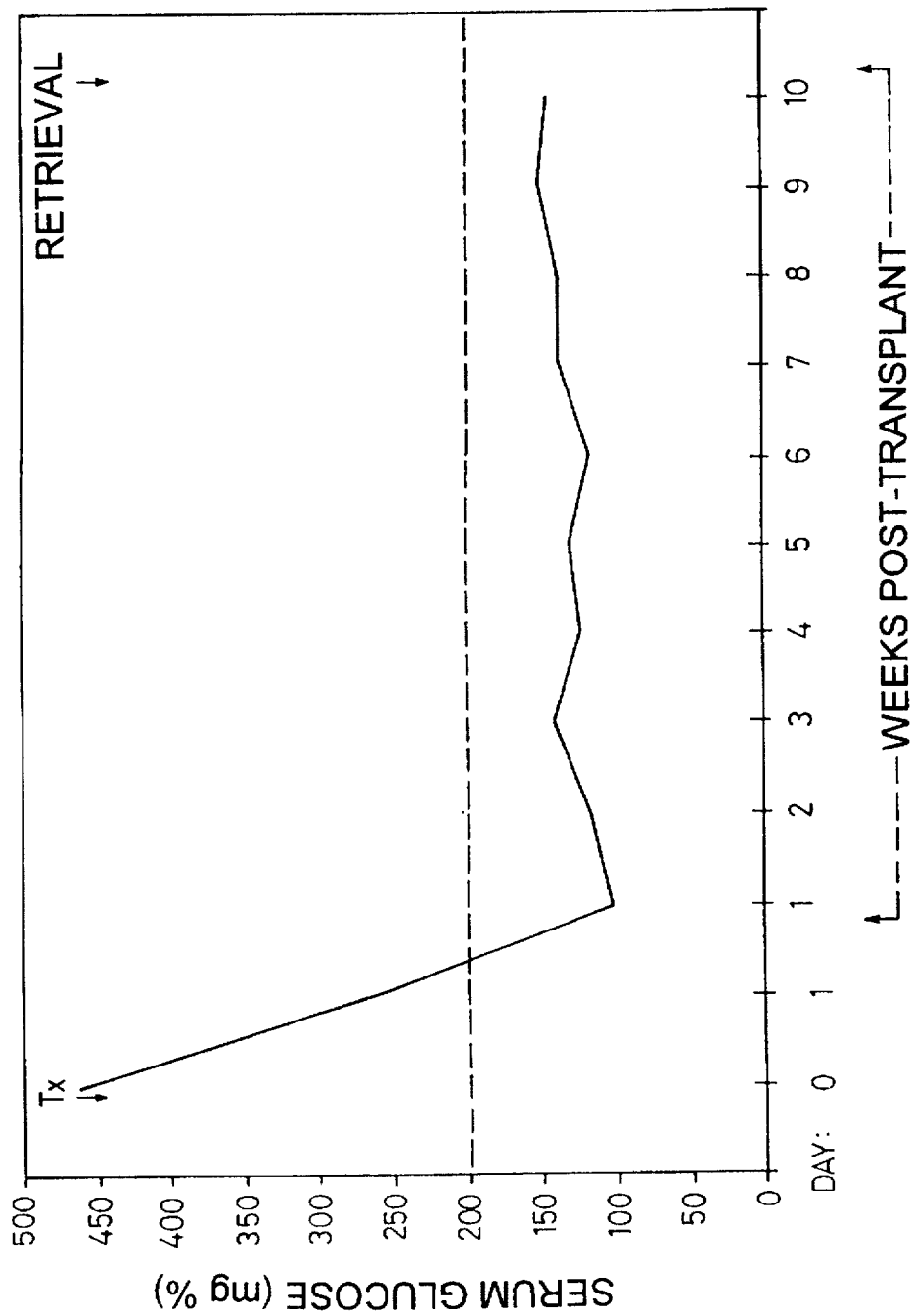
FIG. 3 is a graph demonstrating the viability and effectiveness of islet cells obtained by the invented method, which cells were obtained from rat pancreatic tissue, encapsulated in an alginate capsule and implanted into diabetic rats. This graph shows that the islet cells implanted in the rat kidneys were functional for at least ten weeks.
Figure 4:
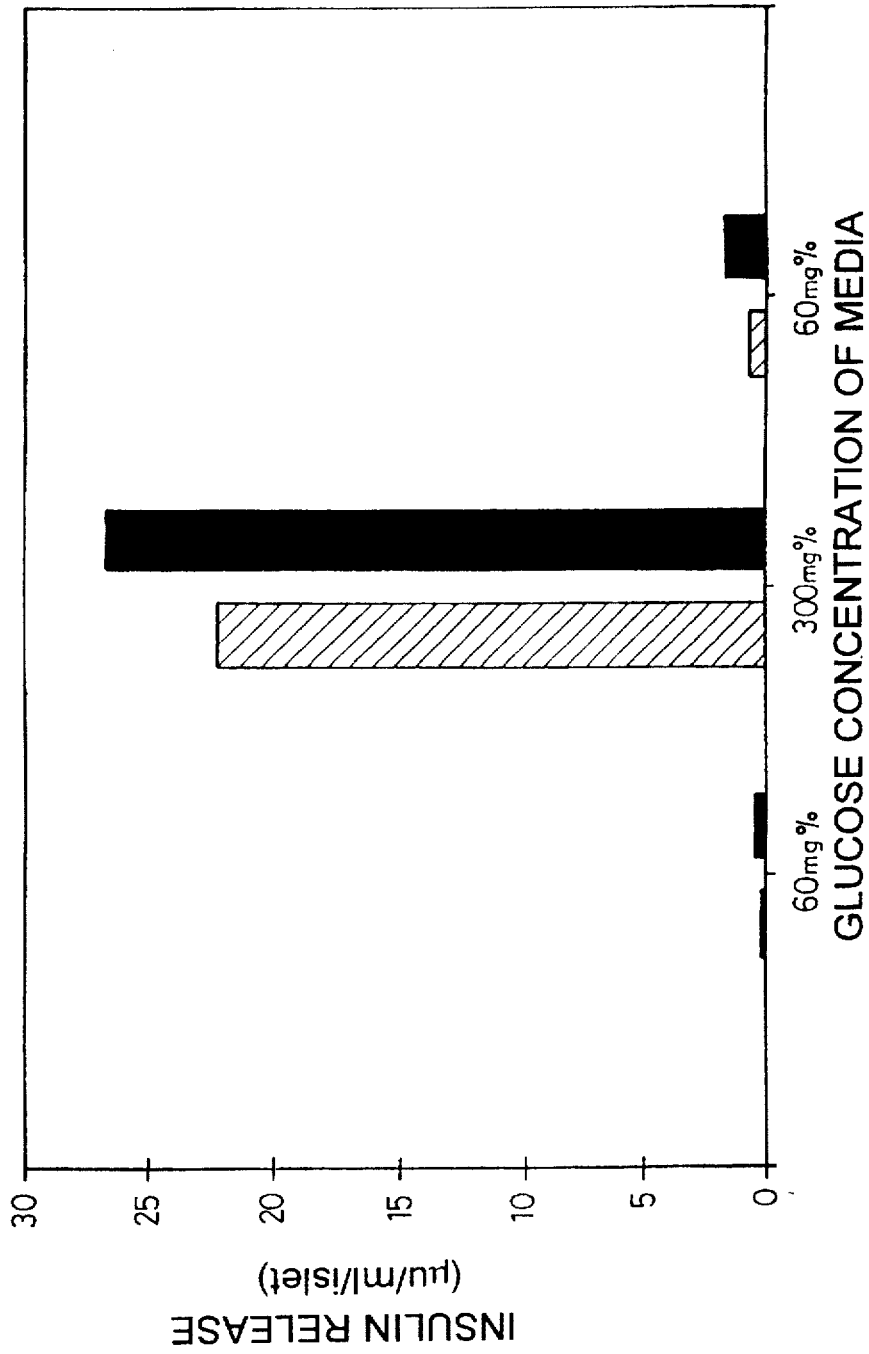
FIG. 4 is a bar graph demonstrating in vitro that the islet cells recovered from the experiment discussed above in connection with FIG. 3 after 75 days of implantation were still reactive to glucose by producing insulin.
Figure 5:
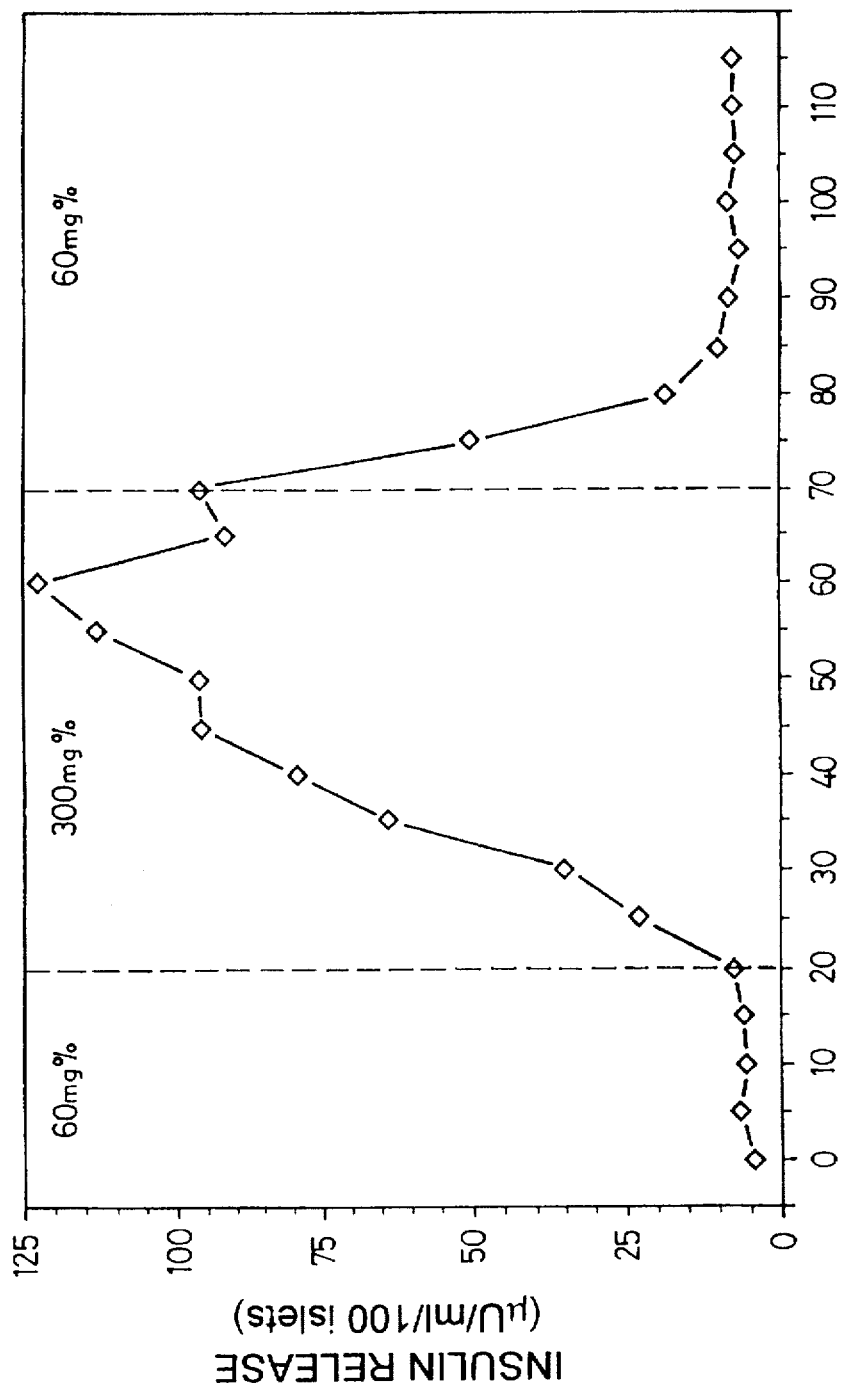
FIG. 5 is a graph also demonstrating the effectiveness of the encapsulated islet cells of the experiments of FIGS. 3 and 4. in vitro by constant perfusion of the encapsulated cells with first 60 mg % and then 300 mg % glucose and then 60 mg % glucose again and the insulin release is measured.

FIGS. 3, 4, and 5 show the result of an experiment wherein rat islet cells purified in accordance with the present invention. The islet cells were encapsulated as discussed above and implanted into diabetic Lewis rats for up to 75 days. FIG. 3 shows that the islet cells functioned for the entire length of the experiment in that the serum glucose levels dropped from over 450 mg % prior to implantation to 100–150 mg % and remained at that level for the 75 days until the experiment was terminated.

The encapsulated cells were then removed from the diabetic rat into which they were transplanted and the function of the islet cells was then tested in vitro. The cells were exposed to 60 mg % glucose, 300 mg % glucose and then 60 mg % glucose and the production of insulin was measured. These results were compared with islets that were tested prior to transplantation. As can be seen from the bar graph, the 300 mg % incubation caused the islets to release substantial amounts of insulin and the post transplanted and pre-transplanted cells functioned nearly the same, and in fact the post transplantation cells functioned slightly better.

In a similar experiment, the results of which are shown in FIG. 5, the post-transplanted islets were perfused with a solution containing varying concentrations of glucose. The cells effectively produced insulin after exposure to 300 mg % glucose and the production of insulin decreased immediately after the glucose concentration in the perfusion medium was decreased to 60 mg % again.

It will be obvious to a person of ordinary skill in the art that the present invention is not limited in its application to the specific materials and methods described as the preferred embodiments herein. The only limitations of the present invention are set forth in the claims appended hereto and any equivalents thereof.

I claim:

1. An aqueous density gradient composition for isolating and purifying pancreatic islets from a population of acinar cells, in which the population had been previously exposed to collagenase through pancreatic ductal injection, by introducing said population containing islets and acinar cells to the composition, said composition comprising:

(A) a first, or lower solution having a density between 1.097 and 1.126 g/ml, and being slightly hypertonic to the islets and acinar cells, said first solution comprising a mixture of a water soluble, metabolically inert substance selected from 5-(N-2,3-dihydroxypropylacetamido) 2,4,5-tri-iodo-N,N'-bis(2,3-dihydroxypropyl) isophthalamide and Metrizamide®, mixed with a physiological cold storage solution selected from University of Wisconsin (UW) solution and Eurocollins;

(B) and a second, or upper solution, having a density of 1.008 g/ml or less, selected from the group consisting of:

(1) a physiological solution capable of maintaining viable cells selected from the group consisting of Hank's solution, RPMI, MEM, and Eagle's medium, and (2) a mixture of a water-soluble, metabolically inert substance selected from 5-(N-2,3-dihydroxypropylacetamido) 2,4,5-ti-iodo-N,N'-bis (2,3-dihydroxypropyl) isophthalamide and Metrizamide, mixed with a physiological cold storage solution selected from UW solution and Eurocollins, overlaid with a physiological solution capable of maintaining viable cells, selected from the group consisting of Hank's solution, RPMI, MEM, and Eagle's medium.

2. The composition according to claim 1, wherein said physiological cold storage solution has a viscosity in the range of about 1.5 to about 2.3 mPa. s.

3. The composition according to claim 1, wherein said first and second solutions have osmolarities in the range of about 320 mOsm to about 440 mOsm.

4. A method of isolating pancreatic islets from a population containing acinar cells, wherein the population containing islets and acinar cells had been previously exposed to collagenase through pancreatic ductal injection, said method comprising:

(A) adding said population of islets and cells to a first or lower solution, said solution having a density between 1.097 and 1.126 g/ml, and being slightly hypertonic to the islets and acinar cells, comprising a mixture of a water soluble, metabolically inert substance selected from 5-(N-2,3-dihydroxypropylacetamido) 2,4,5-tri-iodo-N,N'-bis(2,3-dihydroxypropyl) isophthalamide and Metrizamide®, mixed with a physiological cold storage solution selected from University of Wisconsin (UW) solution and Eurocollins;

(B) layering a second solution, having a density of 1.008 g/ml or less, selected from the group consisting of:

(1) a physiological solution capable of maintaining viable cells selected from the group consisting of Hank's solution, RPMI, MEM, and Eagle's medium, and (2) a mixture of a water-soluble, metabolically inert substance selected from 5-(N-2,3-dihydroxypropylacetamido) 2,4,5-ti-iodo-N,N'-bis (2,3-dihydroxypropyl) isophthalamide and Metrizamide, mixed with a physiological cold storage solution selected from UW solution and Eurocollins, overlaid with a physiological solution capable of maintaining viable cells, selected from the group consisting of Hank's solution, RPMI, MEM, and Eagle's medium;

(C) separating the two cell types by letting the solution sit at 1 g for least 30 minutes, or by applying a centrifugal force up to about 180 g for about 15 minutes at 4° C., to said combination of solutions whereby said islets collect at or near the interface between said first solution and said second solution and said acinar cells accumulate at or near the bottom below said first solution, and (D) removing said islet cells.

5. The method according to claim 4, wherein said physiological cold storage solution has a viscosity in the range of about 1.5 to about 2.3 mPa. s.

6. The method according to claim 4, wherein said first and second solutions have osmolarities in the range of about 320 mOsm to about 440 mOsm.

* * * * *